(12) United States Patent
Hill et al.

(10) Patent No.: US 8,269,196 B2
(45) Date of Patent: Sep. 18, 2012

(54) HEAVY ION RADIATION THERAPY SYSTEM WITH STAIR-STEP MODULATION

(75) Inventors: Patrick M. Hill, Madison, WI (US); Thomas R. Mackie, Verona, WI (US); Jihad H. Al-Sadah, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 274 days.

(21) Appl. No.: 12/439,440

(22) PCT Filed: Feb. 27, 2008

(86) PCT No.: PCT/US2008/055161
§ 371 (c)(1),
(2), (4) Date: Feb. 27, 2009

(87) PCT Pub. No.: WO2008/106532
PCT Pub. Date: Sep. 4, 2008

(65) Prior Publication Data
US 2009/0212231 A1    Aug. 27, 2009

Related U.S. Application Data

(60) Provisional application No. 60/891,859, filed on Feb. 27, 2007.

(51) Int. Cl.
*G21K 5/04* (2006.01)
*G21K 3/00* (2006.01)
*A61N 5/10* (2006.01)

(52) U.S. Cl. .......... 250/492.3; 250/505.1; 378/157; 378/156; 378/158

(58) Field of Classification Search .......... 250/492.3, 250/505.1; 378/156, 157, 158
See application file for complete search history.

(56) References Cited

U.S. PATENT DOCUMENTS

| | | | |
|---|---|---|---|
| 4,276,477 A | 6/1981 | Enge | |
| 5,317,616 A | 5/1994 | Swerdloff et al. | |
| 5,394,452 A | 2/1995 | Swerdloff et al. | |
| 5,442,675 A | 8/1995 | Swerdloff et al. | |
| 5,528,650 A | 6/1996 | Swerdloff et al. | |
| 5,548,627 A | 8/1996 | Swerdloff et al. | |
| 5,625,663 A | 4/1997 | Swerdloff et al. | |
| 5,661,773 A | 8/1997 | Swerdloff et al. | |
| 5,668,371 A | 9/1997 | Deasy et al. | |
| 5,673,300 A | 9/1997 | Reckwerdt et al. | |

(Continued)

FOREIGN PATENT DOCUMENTS

EP    0986070 A    3/2000
(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner* — Jack Berman
(74) *Attorney, Agent, or Firm* — Boyle Fredrickson, S.C.

(57) ABSTRACT

A system for modulating a fan beam for radiation treatment employs shutters that may move rapidly into and out of different beamlets of a fan beam, the shutters having a systematic weighting so that a limited number of shutters may obtain a far greater number of regularly spaced energy reductions.

19 Claims, 8 Drawing Sheets

U.S. PATENT DOCUMENTS

| | | | |
|---|---|---|---|
| 5,724,400 | A | 3/1998 | Swerdloff et al. |
| 5,802,136 | A | 9/1998 | Carol |
| 6,345,114 | B1 | 2/2002 | Mackie et al. |
| 6,385,286 | B1 | 5/2002 | Fitchard et al. |
| 6,438,202 | B1 | 8/2002 | Olivera et al. |
| 6,560,311 | B1 | 5/2003 | Shepard et al. |
| 6,618,467 | B1 | 9/2003 | Ruchala |
| 6,636,622 | B2 | 10/2003 | Mackie et al. |
| 6,661,870 | B2 | 12/2003 | Kapatoes et al. |
| 6,731,970 | B2 | 5/2004 | Schlossbauer et al. |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,207,715 | B2 | 4/2007 | Yue |
| 7,302,038 | B2 | 11/2007 | Mackie |
| 2002/0136439 | A1 | 9/2002 | Ruchala et al. |
| 2003/0160189 | A1 | 8/2003 | Matsuda |
| 2003/0198319 | A1 | 10/2003 | Toth et al. |
| 2005/0123092 | A1 | 6/2005 | Mistretta et al. |
| 2005/0197564 | A1 | 9/2005 | Dempsey |
| 2006/0226372 | A1 | 10/2006 | Yanagisawa |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 | 2/2007 | Lu et al. |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapatoes et al. |
| 2007/0242801 | A1 | 10/2007 | Mackie et al. |

FOREIGN PATENT DOCUMENTS

| | | | | |
|---|---|---|---|---|
| JP | 2000 214298 | A | | 8/2000 |
| JP | 2005024475 | A | * | 1/2005 |
| WO | WO02/07817 | A | | 1/2002 |
| WO | WO02/41948 | A | | 5/2002 |
| WO | WO2005/004168 | A | | 1/2005 |
| WO | WO2007/021226 | A | | 2/2007 |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, Jo, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.

Deasy, JO, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of proton therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-152, Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modem Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anferov V., Combined X-Y scanning magnet for conformal proton radiation therapy, Med. Phys., Mar. 2005, 32:815-818, American Association of Physical Medicine, New York, New York.

Goitlein, M., Beam scanning for heavy charged particle radiotherapy, Nov./Dec. 1983, Med. Phys. 10 (6) pp. 831-840, American Association of Physical Medicine, New York, New York.

* cited by examiner

HEAVY ION RADIATION THERAPY SYSTEM WITH STAIR-STEP MODULATION

CROSS-REFERENCE TO RELATED APPLICATIONS

This application claims the benefit of U.S. Provisional Application 60/891,859, filed Feb. 27, 2007, PCT Application PCT/US2008/055162, filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States government has certain rights in this invention.

BACKGROUND OF THE INVENTION

The present invention relates to radiotherapy systems, such as those using ions (such as protons), for the treatment of cancer and, in particular, to a system providing improved treatment speed and accuracy.

External beam radiation therapy may treat a tumor within a patient by directing high-energy radiation in one or more beams toward the tumor. Highly sophisticated external beam radiation systems, for example, as manufactured by Tomotherapy, Inc., treat a tumor with multiple x-ray fan beams directed at the patient over an angular range of 360°. Each of the beams is comprised of individually modulated beamlets whose intensities can be controlled so that the combined effect of the beamlets, over the range of angles, allows a complex area to be treated.

X-rays deposit energy along the entire path between the x-ray source and the exit point in the patient. While judicious selection of the angles and intensities of the beamlets of x-ray beamlets can minimize radiation applied to healthy tissue outside of the tumor, the inevitability of x-ray irradiation of healthy tissue along the path to the tumor has led to the investigation of ions, such as protons, as a substitute for x-rays. Unlike x-rays, protons may be controlled to stop within the tissue, eliminating exit dose through healthy tissue on the far side of the tumor. Further, the dose deposited by a proton beam is not uniform along the entrance path of the beam, but rises substantially to a "Bragg peak" near a point where the proton beamstops within the tissue. The placement of Bragg peaks inside the tumor allows for improved sparing of normal tissue for proton treatments relative to x-ray treatments.

Current proton therapy systems adopt one of two general approaches. In the first approach, termed the "spread out Bragg peak" (SOBP) approach, the range of energies in the proton beam is expand so that their Bragg peaks extend over a range roughly matching the tumor depth. Precise shaping of this volume is provided by a specially constructed correction range compensator which provides additional range shifting to warp the distal edge of the Bragg peaks to the distal edge of the tumor. This treatment approach can treat the entire tumor at once and therefore is fast. But it is difficult to conform the dose to the tumor volume and the construction of a special range compensator is required.

In a second approach, termed the "magnetic spot scanning" (MSS) approach, the proton beam remains narrowly collimated in a "pencil beam" and is steered in angle and range to deposit the dose as a series of small spots within the patient. The spots are located to cover the tumor in successive exposures until an arbitrary tumor volume has been irradiated. This approach is potentially very accurate, but because the tumor is treated in many successive exposures, this approach is much slower than the SOBP approach. Further the small spot sizes create the risk of uneven dose placement or "cold spots" between the treatment spots, something that is exacerbated if there is any patient movement between exposures.

SUMMARY OF THE INVENTION

The present invention provides a treatment system that uses a fan beam of ions composed of "beamlets" each of which may be separately modulated. In this way the benefits of parallel treatment of different portions of the tumor of SOBP is combined with the benefit of precise control of small portions of the beam of MSS. The modulator uses a set of arrays of energy reducing modulation elements, the arrays subtending the fan beam, and the modulation elements lined up within the beamlets of the fan beam. The modulation elements maybe separately inserted or removed from the beam.

By assigning different weights to each of these modulation elements, a number of regular steps of energy reduction can be obtained that greatly exceed the number of elements. For example, if each element is given a weighting according to a binary power (e.g. 1, 2, 4, 8), then eight shutters may obtain 256 separate energy reduction levels. Unlike movable wedge systems, this "binary shutter system" can jump rapidly between different levels of energy reduction and provide highly repeatable levels without sophisticated feedback control systems. The same modulation system may be used for photon radiation as well, but now the intensity of the beam is reduced, not the energy.

Specifically, then, the present invention provides a modulator for therapeutic radiation having an inlet receiving a fan beam of radiation traveling along an axis and having a cross-sectional area whose greatest dimension extends along a plane. A set of arrays of modulation elements are positioned side by side along the plane within the cross-sectional area and the attenuation elements of the arrays are aligned along the axis. Each modulation element is movable between at least one extended position within the cross-sectional area and a retracted position outside of the cross-sectional area.

A set of actuators communicates with each attenuation element to independently actuate the attenuation elements to move the attenuation elements between two discrete positions, one position out of the fan beam and at least one position in the fan beam. Different attenuation elements presents the beam with variable thickness that is finely controlled. The attenuating thickness provide different reductions in radiation energy so that a series of regular increments of energy reduction can be provided in different portions of the fan beam by selection of different combinations of the attenuation elements for actuation. If the radiation happens to be photons then the variable thickness reduces the intensity of the photons at a specific energy bin.

It is thus an object of one embodiment of the invention to provide an improved fan beam modulator for radiation that can provide high-speed, precise control of adjacent beamlets within the fan.

The actuators may independently actuate the modulation elements to move the elements between only two states, a retracted position outside of the beam and an extended position fully covering the beam.

It is thus another object of one embodiment of the invention to provide a binary shutter system greatly simplifying the control of the actuators.

The energy reduction provided by different attenuation elements may be related according to a binary power sequence.

It is thus an object of one embodiment of the invention to provide a simple modulation sequence providing uniform increments.

Two sets of modulation elements may be positioned in opposition across the plane.

It is thus another object of one embodiment of the invention to provide simultaneous control of two adjacent fan beams.

The attenuation elements of an array may be of uniform material and have different thicknesses within the cross-sectional area when in the extended position providing different reductions in ion beam energy or photon beam intensity.

It is thus an object of one embodiment of the invention to provide for simplified construction with well-characterized homogenous materials.

The modulating elements of different thickness may be ordered within the beam to create jumps in thicknesses deviating from an ordering according to thickness.

It is thus an object of one embodiment of the invention to provide for improved spacing between actuators allowing direct drive of the attenuating elements by the actuators.

Alternatively or in addition the modulating elements of the array may have different densities providing different reductions in ion beam energy or photon beam intensity.

It is thus an object of one embodiment of the invention to provide a more compact shutter system.

The actuators of an array may in combination block the radiation to provide for intensity modulation of the radiation when the radiation is an ion beam.

Thus it is an object of one embodiment of the invention to provide a modulator that may perform both range shifting and modulation of intensity of heavy ion beams.

These particular objects and advantages may apply to only some embodiments falling within the claims and thus do not define the scope of the invention.

DETAILED DESCRIPTION OF THE PREFERRED EMBODIMENT

Figure 1:
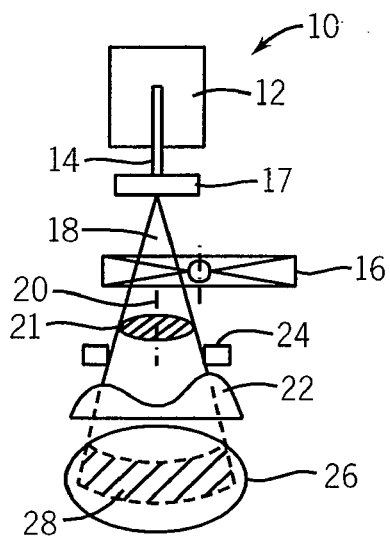
FIG. 1 is a simplified representation of the elements of a prior art radiation therapy system using the SOBP approach described above.

Referring now to FIG. 1, a conventional ion radiation therapy system 10 employing the SOBP approach described above provides an ion source 12 producing a pencil beam 14 of ions traveling along an axis 20.

The pencil beam 14 may be received by a foil 17 scattering the pencil beam into a cone beam 18 having a circular cross-section 21. The energy of the ions in the cone beam 18 is then received by a rotating wedge propeller placing a material of varying thickness in the cone beam 18 and acting as a range shifter 16 continuously changing the energy and thus range of penetration of the ions into tissue.

The cone beam 18 then passes through a collimator 24 approximating the outline of the tumor and a compensator 22 tailor-made for the particular tumor being treated after which the cone beam 18 is received by the patient 26 to produce a treatment pattern 28. As noted, this treatment approach simultaneously treats the entire volume of the tumor and is therefore relatively quick, but requires custom built collimators 24 and compensators 22 and also produces a treatment pattern 28 with imperfect conformance to an arbitrary tumor volume.

Figure 2:
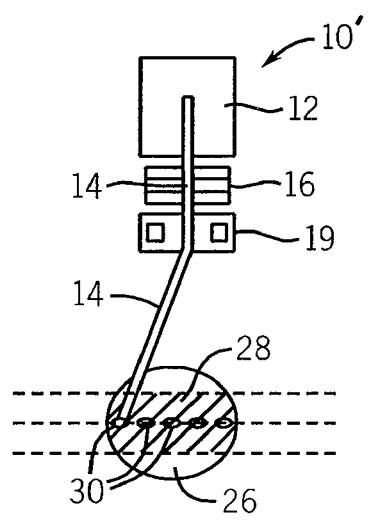
FIG. 2 is a figure similar to that of FIG. 1 showing the elements of a prior art radiation therapy system using the MSS approach described above.

Referring to FIG. 2, a radiation therapy system 10' for implementing the MSS approach, described above, receives a pencil beam 14 from an ion source 12 and passes it through a range shifter 16, for example, a set of movable plastic blocks of different thicknesses. The range shifted pencil beam 14 passes next to a magnetic steering yoke 19 which steers the pencil beam 14 to different spots 30 within the patient 26. Multiple spots 30 together create the treatment pattern 28. This system produces good conformance of the treatment pattern 28 to an arbitrary tumor, but the sequential process is slow.

Figure 3:
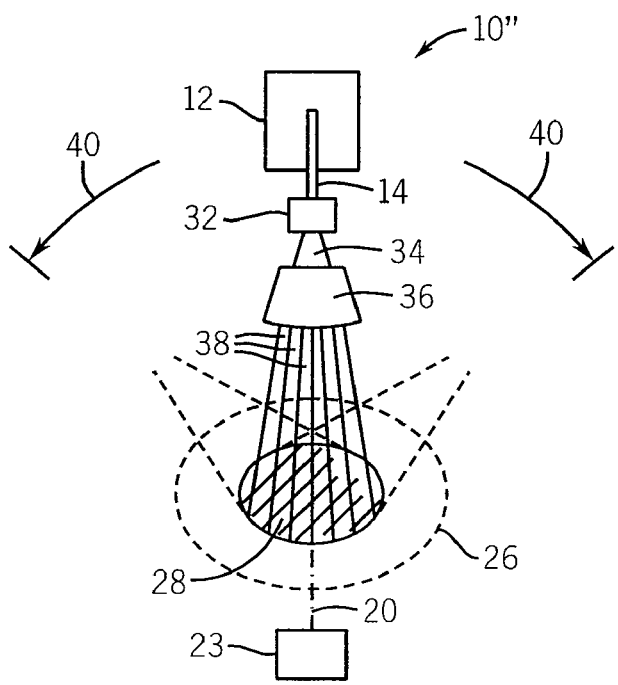
FIG. 3 is a figure similar to that of FIGS. 1 and 2 showing the elements of a fan beam system of the present invention employing a fan beam with individually modulated beamlets and a rocking exposure pattern.

Referring now to FIG. 3, the radiation therapy system 10" of the present invention employs an ion source 12 producing a pencil beam 14. In a preferred embodiment, the pencil beam 14 is received by a magnetic beam former 32 converting the pencil beam 14 into a fan beam 34 by magnetic deflection rather than scattering and thus minimizing the generation of neutrons.

The fan beam 34 is next received by a binary shutter system 36 which individually modulates the range and the intensity of the individual beamlets 38 of the fan beam 34, the beamlets 38 being adjacent sectors of that fan beam 34. The modulated fan beam 34 may be moved in a partial arc 40 with respect to the patient 26 to provide for complex treatment patterns 28 taking advantage both of multiple angles of treatment and the ability to individually control the intensity and range of the beamlets 38.

Figure 4:
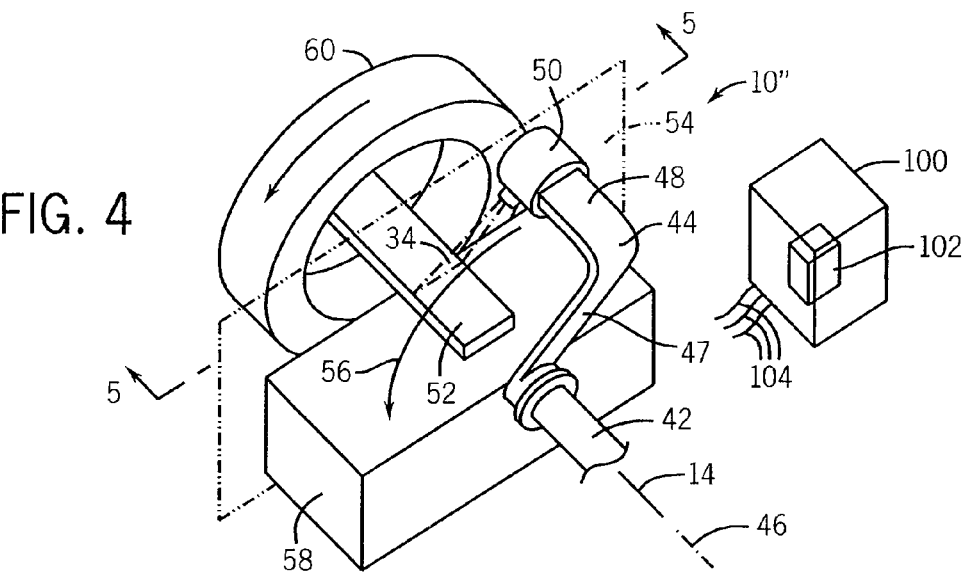
FIG. 4 is a perspective view of an ion therapy machine incorporating the elements of FIG. 3 providing constrained rotation of the fan beam.

Referring now to FIG. 4, the structure of the radiation therapy system 10" may provide, for example, an axial proton beam conduit 42 receiving the pencil beam 14 of protons, for example, from a remote cyclotron or synchrotron (not shown).

Beam steering magnets of a type well known in the art (not shown) may bend to the pencil beam 14 to follow a "crank arm" path of a gantry 44 having a radially extending segment 47 passing on a line of radius from an axis 46 of the entering pencil beam 14 and an axial segment 48 parallel to the axis 46 but spaced from the axis 46 as attached to the end of the radially extending segment 47. The distal end of the axial segment 48 holds a gantry head 50 (whose elements are shown generally in FIG. 3) and which directs a fan beam 34 toward a patient support 52, the latter generally aligned with the axis 46.

The fan beam 34 lies generally within a plane of rotation 54 of the gantry head 50 as the gantry head 50 moves about the patient support 52. By aligning the axis of rotation of the gantry head 50 with the axis 46 of the entering pencil beam 14, constant field bending magnets within the gantry 44 may channel the pencil beam 14 to the gantry head 50 at any of its angular positions.

Figure 5:
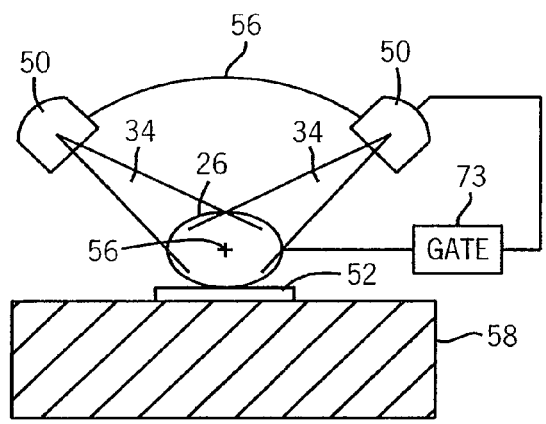
FIG. 5 is a cross-section taken along line 5-5 of FIG. 4 showing the range of motion of a center axis of the fan beam in the present invention with respect to stationary neutron shield.

Referring momentarily to FIG. 5, the gantry head 50 may rotate in an arc 56 about the axis 46 by an amount substantially less than 180° and in the preferred embodiment approximately 150°. As will be described further below, the present inventors have determined that this limited rotation, un-intuitively, can provide a superior dose pattern 28 when compared to a more complete 360° rotational of the gantry head 50, such as would be preferred for intensity modulated radiation therapy using photons.

The limited range of arc 56 allows a massive stationary neutron stop 58 to be placed under the patient support 52 to receive neutrons generated by interaction of the ions with the patient 26 over the full range of arc 56. The ability to use a stationary neutron stop 58, allows the neutron stop 58 to be larger and closer to the patient 26, allowing, for example, a form in-place concrete neutron shield.

Figure 6:
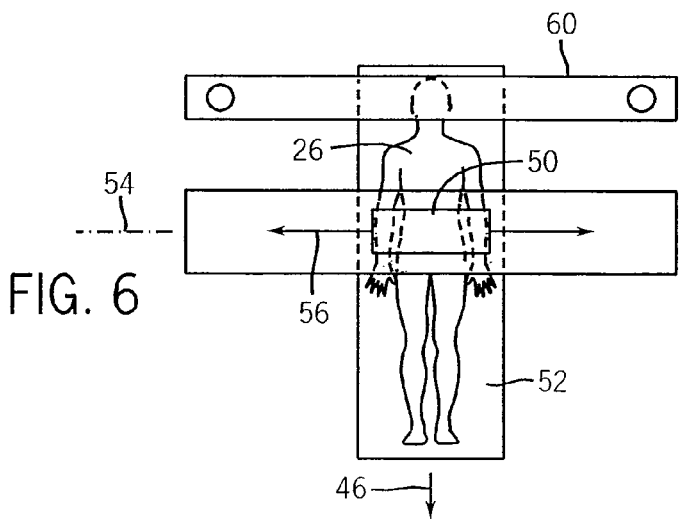
FIG. 6 is a top plan view in phantom of the system of FIG. 5 showing positioning of a patient to be pre-scanned with a tomography ring and then treated using the present invention.

Referring now to FIGS. 4 and 6, an x-ray tomography ring 60 may be placed adjacent to the neutron stop 58 along the axis 46 so as to provide for planning tomographic images of the patient 26 contemporaneous with the radiation treatment. The displacement of the x-ray tomography ring 60 from the plane of rotation 54 allows a full 360° of access to the patient (generally required of an x-ray tomography machine) for supporting both the detector and opposed x-ray source on opposite sides of the patient.

Figure 7A:
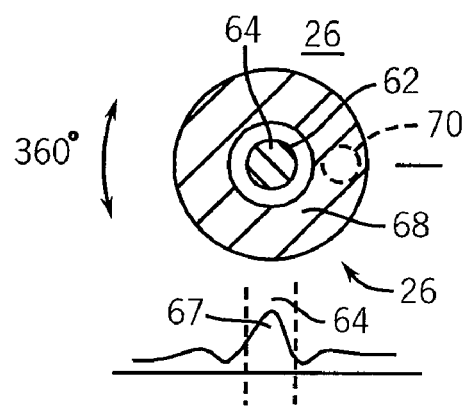
FIGS. 7a and 7b are simplified representations of cross-sectional dose patterns for treatment of a tumor generated with a 360° scan and generated with a 150° scan per one embodiment of the present invention showing the latter scan's superior protection of sensitive distal tissue.
Figure 7B:
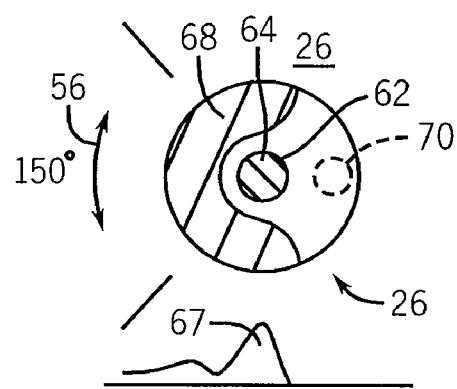

Referring now to FIGS. 7a and 7b, a simplified treatment plan may be developed to treat a tumor 62 in the patient 26 having circular cross-section. Such a plan implemented with ion beam exposure over 360° provides a central region 64 of a dose pattern 28 having a high dose value resulting from aligned Bragg peaks 67 of ion beams entering the patient 26 over a range of angles of 360° about the patient. This central region 64 is surrounded by a fringe 68 resulting from a reduced but measurable entrance dose of these proton beams. This fringe 68 can be problematic if there is radiation sensitive tissue 70, as is often the case, directly adjacent to the tumor 62.

As shown in FIG. 7b, a constrained rotation of the gantry head 50 and hence the fan beam 34 can substantially limit the fringe 68 while preserving good conformity between the central region 64 and the tumor 62. The ability to stop the ions within the tissue at the Bragg peak 67 can wholly spare the radiation sensitive tissue 70. The present inventors have determined that the limitation of the arc 56 to as little as 150° still provides close conformance of the shape of central region 64 to the tumor 62 and minimization of hot/cold spots.

Figure 8:
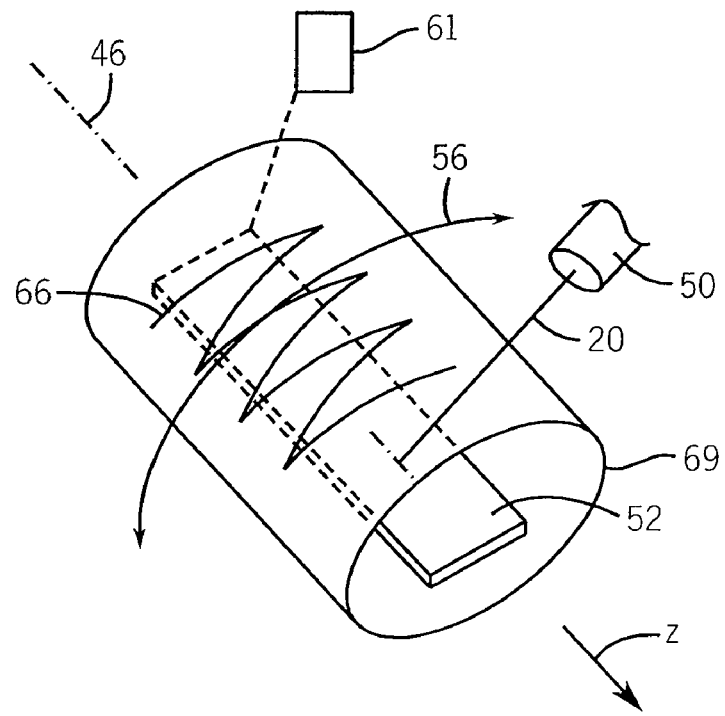
FIG. 8 is a perspective view of a "semi-helical" scanning pattern that may be implemented with the present invention.

Referring now to FIG. 8, the limited width of the fan beam along axes 46 makes it desirable to translate the patient support 52 along axes 46 with respect to the gantry head 50 in order to obtain treatment volumes matching the longitudinal extent of the tumor while still preserving good spatial resolution determined by the thickness of the fan beam. The table may be translated by a table translation mechanism 61 such as a motorized carriage moving the patient support 52 or the gantry head 50 or both.

In one embodiment of the present invention, the translation of the patient support 52 may be continuous as the gantry head 50 rocks back and forth over the treatment arc 56 in a so-called "semi-helical" scan pattern such as traces a sawtooth raster 66 along axes 46 on an imaginary cylinder 69 surrounding the axis 46.

Figure 9:
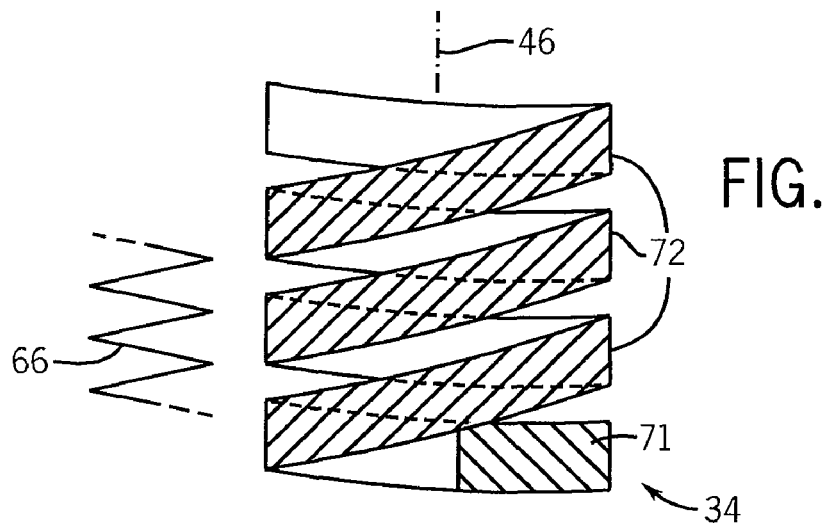
FIG. 9 is a top plan view of the helical scan of FIG. 8 showing overlap of the scans that provides for "re-painting" reducing hot spots/cold spots.

Referring now to FIG. 9, a sweeping of the cross-sectional area 71 of the fan beam 34 in this semi-helical scan pattern may be given a "pitch" by changing the relative speed of movement of the patient support 52 with respect to the speed of movement of the gantry head 50 in each cycle of reciprocation. The pitch determines the degree of overlap between successive sweep paths 72 of the sawtooth raster 66 moving cross-sectional area 71, such overlap serving to reduce hotspots. The pitch shown here is greatly exaggerated and, in practice, would be reduced to a fraction of the width of the cross-sectional area 71 along axes 46. The scanning of the cross-sectional area 71 serves also to eliminate inhomogeneities in the treatment caused by gaps between shutters used to modulate the beamlets 38 as will be described below.

Figure 10:
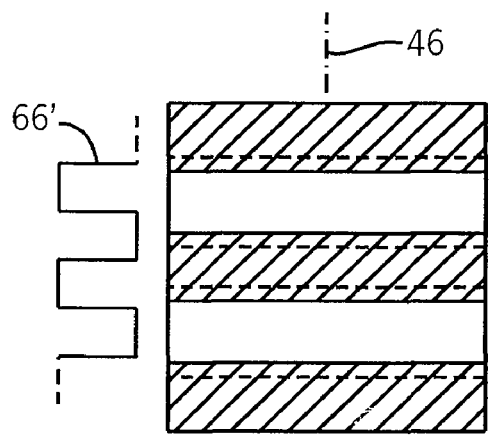
FIG. 10 is a figure similar to that of FIG. 9 showing an alternative rectilinear scan system.

Referring now to FIG. 10, alternatively a rectilinear raster 66' may be adopted where the gantry head 50 is allowed to complete one half of a cycle of its reciprocation about axis 46 and then is stopped at the limits of the arc 56 to allow translation of the patient 26 along axes 46. When movement of the patient 26 is complete the next cycle of reciprocation along arc 56 is performed.

Figure 11:
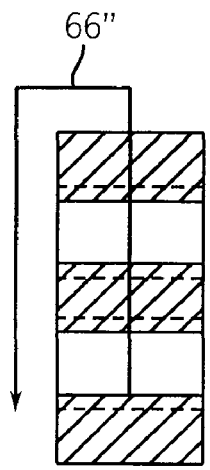
FIG. 11 is a figure similar to that of FIGS. 9 and 10 showing an alternative rectilinear scan that may be superior for motion gating.

Referring now to FIG. 11 and FIG. 5, motion gating may be incorporated into the radiation therapy system 10″ of the present invention in which a sensor system 73 senses movement of the patient 26 or internal organs of the patient 26 (for example, using ECG or respiration signals) to turn the fan beam 34 from the gantry head 50 on and off to treat the patient 26 at a constant phase of periodic motion. This gating process may be improved with a rectilinear raster 66″ shown in FIG. 11, essentially rotating the rectilinear scanning pattern of FIG. 10 so that a full range of translation of the patient support 52 is completed before moving the gantry head 50 incrementally along arc 56.

Figure 12:
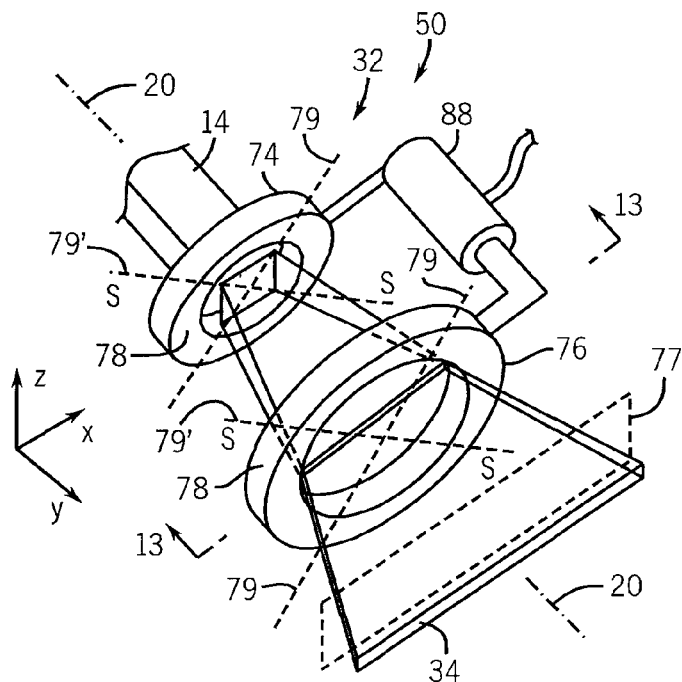
FIG. 12 is a perspective view of a magnetic beam former using two sequential and aligned quadrupole magnet systems and showing a mechanism for adjusting the separation of those magnet systems to adjust the resulting fan beam.

Referring now to FIG. 12, the magnetic beam former 32 (shown in FIG. 1) in a preferred embodiment may comprise two quadrupole magnet assemblies 74 and 76 receiving the pencil beam 14 (as delivered to the gantry head 50 along gantry 44). The pencil beam 14 is first received by a first quadrupole magnet assembly 74 and then received by the second quadrupole magnet assembly 76 downstream from the first quadrupole magnet assembly 74. Both quadrupole magnet assemblies 74 and 76 include apertures 78 coaxially aligned along a center axis 20 of the pencil beam 14 and the fan beam 34.

Figure 13:
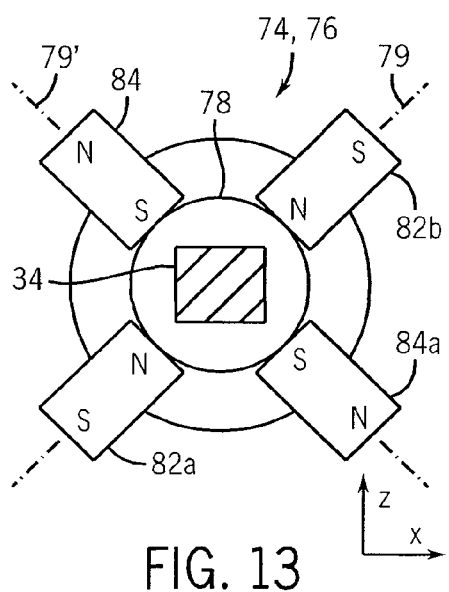
FIG. 13 is a simplified cross-sectional view along 13-13 through one quadrupole magnet of FIG. 12 showing the magnet orientations.
Figure 14:
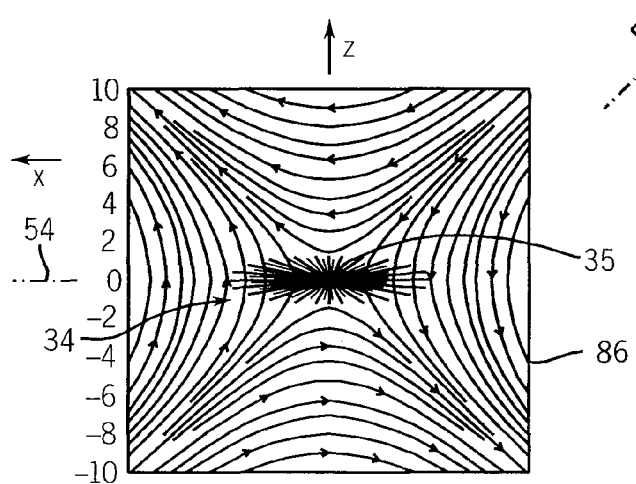
FIG. 14 is a magnetic field map of the quadrupole of FIG. 13.

Referring momentarily to FIGS. 13 and 14, quadrupole magnets of the type used in quadrupole magnet assemblies 74 and 76 are well known in the fields of high-energy accelerator physics and electron microscopy where quadrupole magnets with relative rotations of 90° about the axis of the beam are used to help refocus a pencil beam 14 to maintain its narrow cross-section. Each quadrupole magnet assembly 74 and 76 comprises two pairs of magnets: a first pair 82a and 82b opposed across the aperture 78 along axes 79 with facing north poles, and a second pair 84a and 84b opposed across the aperture 78 along axes 79′ perpendicular to axes 79. The magnets may be permanent magnets or preferably electromagnets so that the field strengths may be varied to allow the width and intensity profiles of the resultant fan beam 34 to be varied in both the convergent and divergent planes.

Referring again to FIG. 12, two quadrupole magnet assemblies 74 and 76 are aligned with respect to each other so that axes 79′ of quadrupole magnet assembly 74 lies in the same plane as axes 79′ of quadrupole magnet assembly 76 (this plane also including axis 46) and so that axes 79 of quadrupole magnet assembly 74 lies in the same plane as axes 79 of quadrupole magnet assembly 76.

Figure 15:
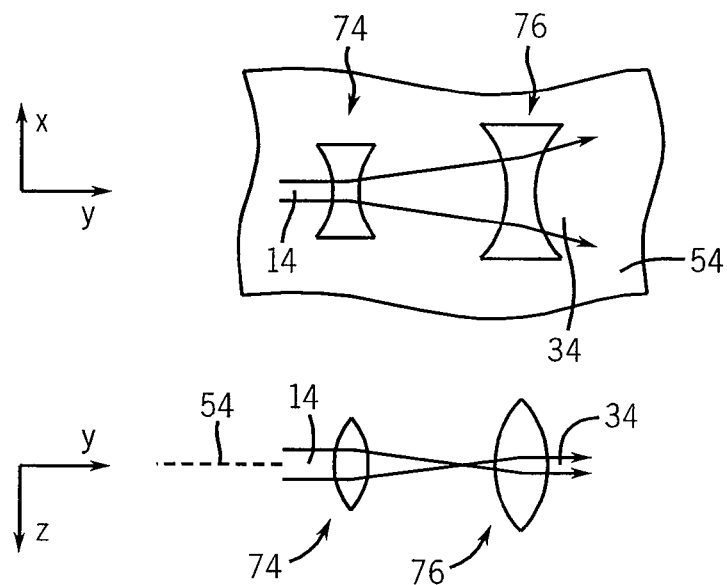
FIG. 15 is an aligned top plan and side elevation view of the beam of FIG. 12 showing the effective operation of the quadrupole magnets as both converging and diverging lenses in different axes.

Referring to FIGS. 6, 14 and 15, the quadrupole magnet assemblies 74 and 76 produce a magnetic field 86 that tends to widen a cross-section 35 of the fan beam 34 along the plane of rotation 54 and compress it in a z-direction normal to the plane of rotation 54.

As shown in FIG. 15, quadrupole magnet assemblies 74 and 76 act like diverging lenses when viewed in the plane of rotation 54 and converging lenses when viewed across the plane of rotation 54. Because the forming of the pencil beam 14 into a fan beam 34 is done without scattering in a solid material, the production of neutrons is largely eliminated.

Note the quadrupole system will work for heavy ions of either polarity with a simple reversal of dimensions.

Referring again to FIG. 12, the quadrupole magnet assemblies 74 and 76 may be connected by controllable actuator mechanism 88 (such as a motor and rack and pinion mechanism) that may separate each of the quadrupole magnet assemblies 74 and 76 along the axis 20 according to an electrical signal and/or by mechanical adjustment. This controllable separation allows adjustment of the cross-sectional dimensions of the fan beam 34 to reduce collimation that also produces neutrons. The ability to change the cross-sectional dimensions of the fan beam 34 without collimation further allows for better utilization of the fan beam energy. The adjustment of the fan beam size may also be used for dynamic change of the beamlets 38 during treatment.

Figure 16:
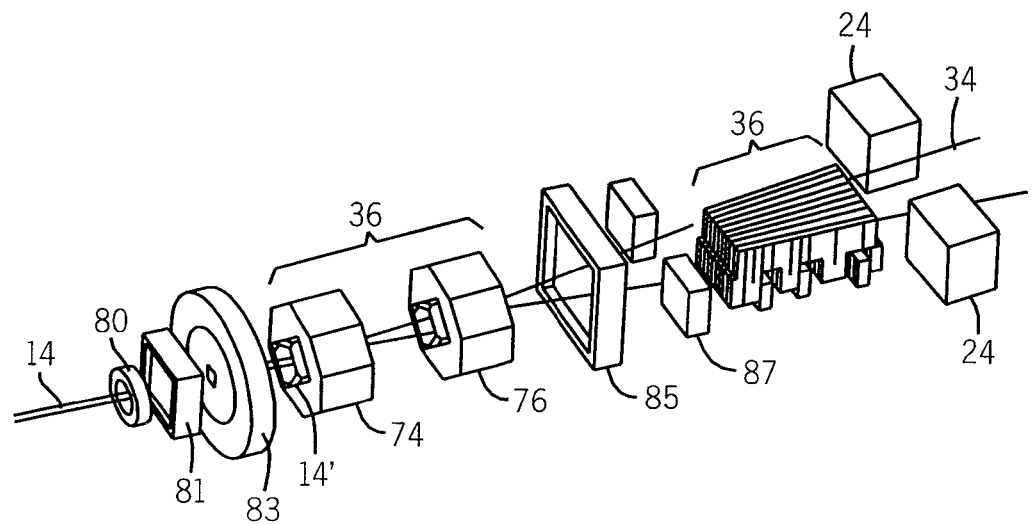
FIG. 16 is a perspective view of the elements of FIG. 3 showing the two quadrupole magnets and a binary shutter system that may be used to generate and modulate the fan beam in the present invention.

Referring now to FIG. 16, the pencil beam 14, ultimately received by the magnetic beam former 32 (composed of quadrupole magnet assemblies 74 and 76) may first pass through an emergency beam stop 80 and an entrance dose monitor 81 of conventional design, the latter measuring the energy of the beam 14. A pencil beam aperture collimator 83 may then shape the pencil beam 14 into a predictable cross-section for receipt by quadrupole magnet assembly 74. After exiting from quadrupole magnet assembly 76 the fan beam 34 may pass through a segmented monitor measuring an energy or intensity profile of the beam 34 that may be used to further correct the energy profile of the fan beam 34 (by compensation using the binary shutter system 36 as will be described) or to correct a cross-section of the fan beam 34, for example by controlling the field strengths of electromagnets of the quadrupole magnet assemblies 74 and 76. The fan beam 34 is then received by a set of collimator blocks 87 sharpening the edges of the fan beam to conform with a binary shutter system 36 as will be described below.

Figure 17:
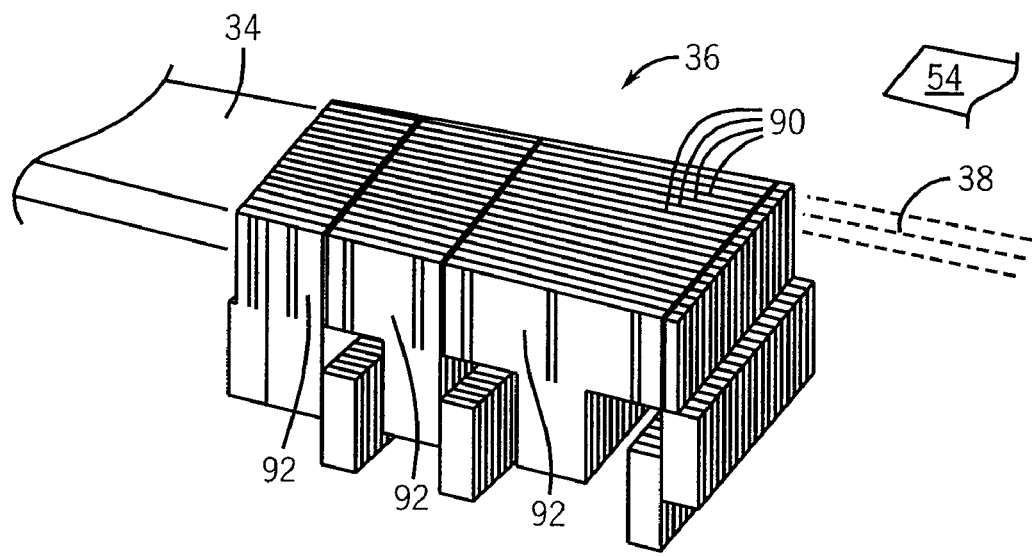
FIG. 17 is a side view of the binary shutter system showing a side-by-side arrangement of arrays of attenuation elements providing shutters.

Simulations have been performed modeling a 235 MeV proton beam traversing two quadrupole magnet assemblies 74 and 76 having effective lengths of 20 cm and 40 cm with transverse gradients of 22 T/m and 44 T/m respectively and a center-to-center quadrupole separation of 50 cm. The results of these simulations indicate that a proton fan beam of suitable cross-section ($40\times2$ cm$^2$) can be generated from an entrant Gaussian beam of protons (1.5 cm FWHM) over a distance of 1.5 m. Referring now to FIGS. 16 and 17, the binary shutter system 36 may provide a set of attenuating arrays 90 each aligned with a separate beamlet 38 of the fan beam 34. Each attenuating array 90 may be composed of a set of attenuating elements 92 (blade) each attenuating element 92 of a single array 90 being aligned with a particular beamlet 38. Multiple arrays 90 are placed side by side to span the width of the fan beam 34 so that each beamlet 38 may be controlled independently by a different array 90.

Figure 18:
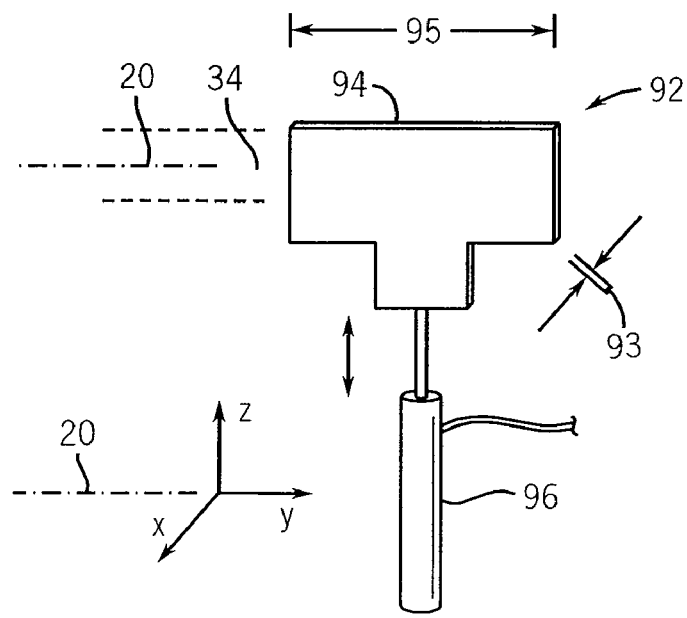
FIG. 18 is a side elevational view of one attenuation element showing its actuator for moving the attenuation element between a retracted position outside of the beam and an extended position within the beam.

Referring now to FIG. 18, each attenuating element 92 comprises blade 94 of an energy absorbing material having a width 93 approximating the angular width of a beamlet within the plane of rotation 54 and a variable effective thickness 95 that will differ for different blades 94 as will be described. The term "effective thickness" is intended to include blades of different materials and different thickness that nevertheless operate as if they were of equal thicknesses of a single material. The blade 94 is attached to an actuator 96 that may move the blade 94 up and down along the y-axis generally perpendicular to the central axis 20 of the fan beam 34. In a preferred embodiment, the blade 94 may be moved between two positions, one within the path of the fan beam 34 and the other completely removed from the path of the fan beam 34. With this "binary" motion the actuator 96 may be extremely simple, for example, a pneumatic piston and cylinder (controlled by fluid pressure controlled in turn by a valve mechanism not shown) or electrical solenoid directly controlled by an electrical circuit.

Figure 19:
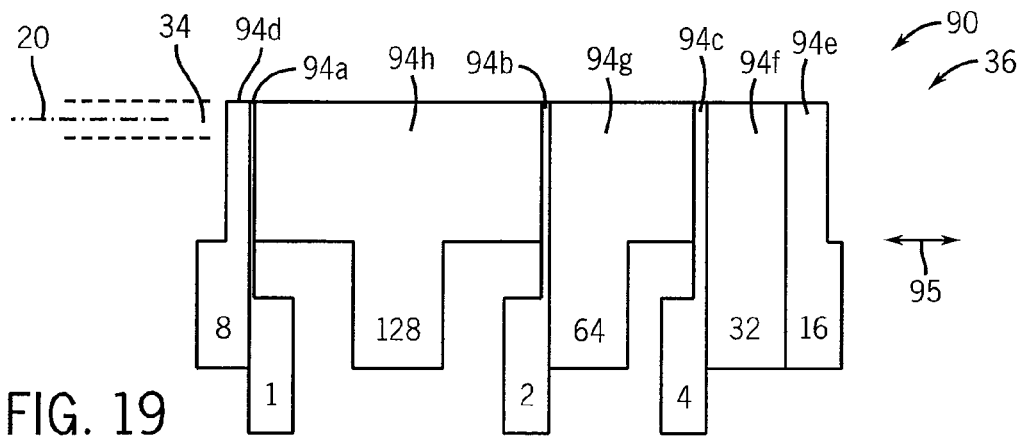
FIG. 19 is a simplified representation of one array of binary-weighted attenuation elements fully extended to block the beam.
Figure 20:
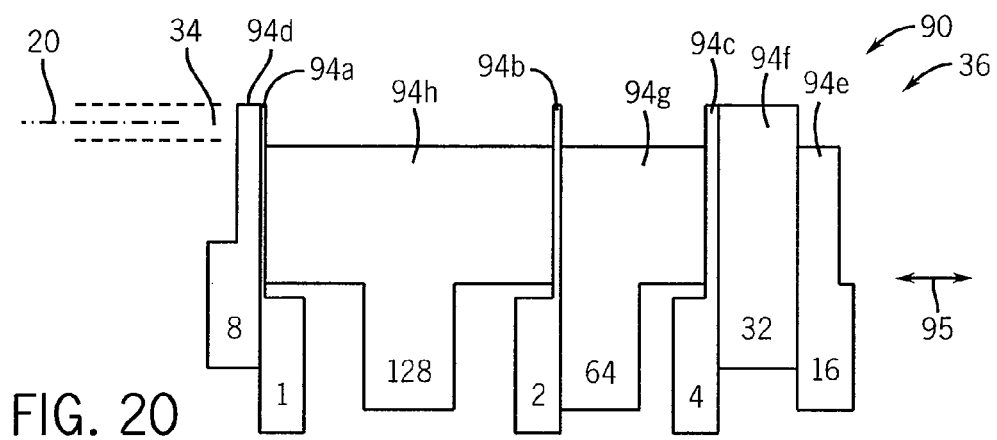
FIG. 20 is a figure similar to that of FIG. 19 showing selected retraction of the attenuation elements such as it may provide controlled energy reduction in the beam.

Referring now to FIG. 19, a single array 90 may, for example, contain eight attenuating elements 92 having blades 94a-94h. In a first embodiment, the effective thickness 95 of each blade 94a-94h along axis 20 may be according to a binary power series so, for example, blade 94a through 94h will have relative effective thicknesses 95 corresponding to successive terms in a binary power sequence (e.g.: 1, 2, 4, 8, 16 etc.). Thus, for example, blade 94*d* may be eight times as thick as the thinnest blade 94*a*. In this way, as shown in FIG. 20, any one of 256 equal increments of attenuation may be obtained by drawing some of the blades 94 out of the beam 34 and placing some of the blades 94 into the beam. In the example of FIG. 20, a relative attenuation of 43 may be obtained consisting of the combined blades 94*d*, 94*a*, 94*b*, and 94*f* (having attenuation's 8, 1, 2, and 32 respectively where 1 is the attenuation provided by the thinnest blade 94*a*). This "binary" sequence must be distinguished from the "binary" action of the shutters and a binary sequence need not be used for the binary shutter system 36 as will be described below.

This binary power series provides the simplest blade structure and actuation mechanisms but it will be understood that other power series can also be used and in fact the variations in attenuations among blades 94 need not conform to a power series but, for example, may conform to other series and may include duplicate blades 94 of a single attenuation, for example to operate at higher speed or distribute wear. For example, the blades 94 may have the relative effective thicknesses 95 of 1, 1, 3, 6, 9, 18, etc.

Alternatively blades 94 positionable in any of three (or more) positions with respect to the fan beam 34 (and hence capable of providing three effective attenuation levels per attenuating element 92) could be used providing attenuations in the series (0, 1, 2), (0, 3, 9), (0, 9, 18), (0, 27, 54) . . . .

It will be further understood that attenuating elements 92 need not be constructed of a uniform material in which their effective thicknesses 95 corresponds to attenuation, but may be constructed of different materials having different densities to minimize their differences in effective thickness 95 for mechanical or structural reasons. The order of the blades 94 in the fan beam 34 need not conform to their relative ranking in attenuation, and in fact in the preferred embodiment this order is buried so as to provide for suitable clearance for the attached actuators 96.

In a preferred embodiment the combination of all attenuating elements 92 completely stops the fan beam 34, and thus a proper selection of different attenuating elements 92 (short of blocking the fan beam 34) may be used to control range shifting of ions of the fan beam 34, while a selection of all attenuating elements 92 (fully blocking the fan beam 34) may be used to control the intensity of the beam through duty-cycle modulation so that both range and intensity may be controlled with the modulator 36. Alternatively a separate blocking element (not shown) for each beamlet 38 may be used to provide this intensity modulation. The intensity modulation or range shifting effected by the binary shutter system 36 may be augmented by other mechanisms applied to some or all of the beamlets 38, for example those correcting the profile of the fan beam 34 or serving to offset the range shifting of all the beamlets 38 based on patient size.

The control of the individual blades 94 may be performed, for example, so that all of the attenuating blades 94 do not move simultaneously but are rather staggered to ensure the minimum deviation in range shifting during the transition of the blades 94. Thus, for example, the movement of blades 94 providing greater attenuation may be alternated with movement of blades 94 providing less attenuation to reduce variations in range shifting.

Figure 21:
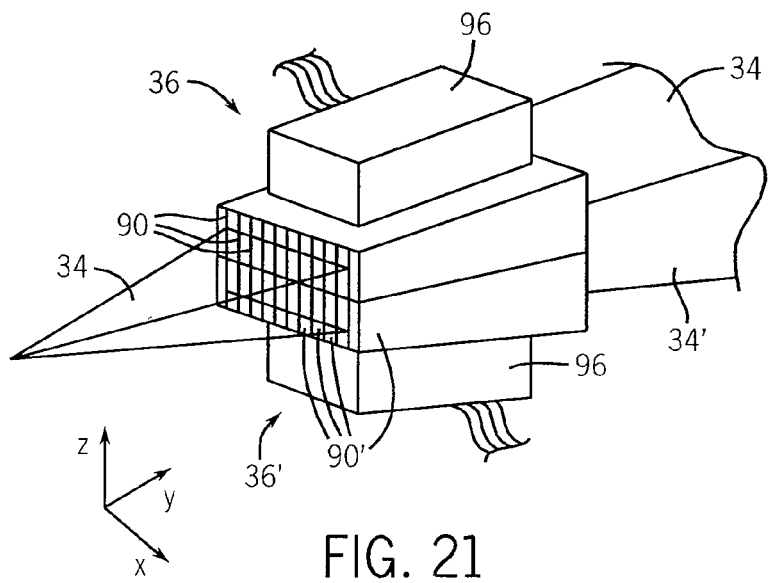
FIG. 21 is an alternative embodiment showing the use of two modulation systems face to face to provide for two independently modulated adjacent fan beams.

Referring now to FIG. 21, two binary shutter systems 36 and 36' may be opposed about the fan beam 34 effectively dividing the fan beam 34 along an x-y plane (parallel to the plane of rotation 54) into two separately modulated fan beams 34 and 34' effectively allowing multi-slice treatment of the patient improving the speed/resolution trade-off of the treatment system. In this case the geometry of the actuators 96 and blades 94 allows all of the actuators 96 to be fully displaced out of the area of the beam 34.

The binary shutter system 36 may also be used for photon modulation; the term "radiation" as used herein will include generally both photons and particles serving for treatment of tissue.

Referring again to FIG. 4, an electronic computer 100 executing a stored program may be associated with the radiation therapy system 10" executing a radiation treatment plan that coordinates and controls all of the electrically controllable elements described above including but not limited to the binary shutter system 36, the magnetic beam former 32 (including magnetic field strength of the magnets and their separation) and the movement of the gantry 44 and patient support 52 as well as receipt and control of the x-ray tomography ring 60. This control may be done according to a stored radiation treatment plan, and in light of signals obtained from monitors 81 and 85. Data collected by the computer 100 then provide images for the assessment of the treatment plan, as well as inputs to feedback loops confirming the proper operation of the system according to techniques known in the art of intensity modulated radiation therapy.

During the movement of the gantry head 50 with respect to the patient support 52, the range and intensity of individual beamlets 38 will be modulated according to a treatment plan stored in the computer 100 and typically determined by a health care professional using an image of the tumor using the tomography ring 60. Determination of the proper modulation of the beamlets 38 may be done by techniques analogous to those used with prior art intensity modulated radiation therapy adapted to the unique properties of ion beams. These techniques include for example Simulated Annealing and gradient based optimization techniques.

The present invention has been described in terms of the preferred embodiment, and it is recognized that equivalents, alternatives, and modifications, aside from those expressly stated, are possible and within the scope of the appending claims.

The invention claimed is:

1. A therapeutic radiation modulator comprising:
an inlet receiving a fan beam of radiation movable over a range of angular positions about a patient, and comprised of adjacent beamlets traveling along axes, the fan beam having a cross-sectional area perpendicular to a propagation of the radiation whose greatest dimension extends along a plane and whose least dimension defines a fan beam thickness;
a set of arrays of modulation elements, the arrays positioned side-by-side along the plane, the modulation elements of each array aligned with a different beamlet, each modulation element movable along the fan beam width between an extended position extending fully through the fan beam width and a retracted position outside of the fan beam;
a set of bistable actuators communicating with each modulation element to independently actuate the modulation elements to move them only to the extended or retracted positions at each discrete angular position during movement of the fan beam over the range of angular positions about the patient;
a control system communicating with each bistable actuator to independently activate the bistable actuators;
wherein different modulation elements provide predetermined effective thicknesses so that a series of regular increments of energy reduction can be provided in different beamlets of the fan beam by selection of different combinations of the modulation elements for actuation; and wherein the modulation elements of each array provide a sequence of increasing effective thicknesses combinable to provide the regular increments of energy attenuation.

2. The therapeutic radiation modulator of claim 1 wherein the bistable actuators independently actuate the modulation elements to move the modulation elements between only two states, a retracted position outside of the beamlet cross-section and an extended position to fully block the beamlet cross-section.

3. The therapeutic radiation modulator of claim 1 wherein the radiation is selected from the group consisting of photon radiation and ion radiation.

4. The therapeutic radiation modulator of claim 1 wherein the sequence of increasing effective thicknesses is a binary power series.

5. The therapeutic radiation modulator of claim 1 wherein the modulation elements have equal thicknesses.

6. The therapeutic radiation modulator of claim 1 further including two sets of modulation elements positioned in opposition across the plane.

7. The therapeutic radiation modulator of claim 1 wherein the modulation elements of an array are of uniform material and have different thicknesses along the axes within the beamlet cross-sectional area of one beamlet when in the extended position, providing different reductions in radiation.

8. The therapeutic radiation modulator of claim 1 wherein the modulation elements of different thicknesses are ordered within the beam to create jumps in thicknesses between successive modulation elements deviating from an ordering according to thickness.

9. The therapeutic radiation modulator of claim 1 further wherein the modulation elements of an array have different densities providing different reductions in radiation.

10. The therapeutic radiation modulator of claim 1 wherein the modulation elements of an array may in combination completely block the radiation to provide for intensity modulation of the radiation through duty-cycle modulation of the bistable actuators.

11. The method of claim 1 wherein a distance between the extended position and the retracted position is equal to a length of the beam cross-sectional area covered by the modulation element when in the extended position.

12. A method of modulating an ion beam comprising:
(a) receiving a fan beam of ions rotating over a range of angular positions about a patient, and traveling along an axis, the fan beam having a cross-sectional area perpendicular to a propagation of the ions whose greatest dimension extends along a plane and whose least dimension defines a fan beam thickness, the fan beam providing a plurality of beamlets positioned side by side in the plane;

(b) positioning a set of arrays of modulation elements so that the modulation elements of each array are spaced along the axis, wherein each modulation element is movable substantially perpendicularly to the plane between an extended position within a beamlet cross-sectional area of one corresponding beamlet and a retracted position outside of the beamlet cross-sectional area of one corresponding beamlet, and so that the arrays of modulation elements are positioned adjacent to each other perpendicular to the axis wherein the modulation elements for each array together provide a sequence of increasing effective thicknesses combinable to provide regular increments of energy attenuation, wherein the area of the fan beam obstructed by each modulation element in the extended position defines a corresponding beamlet; and (c) controlling a set of bistable actuators communicating with each modulation element to independently control the modulation elements to move them only to the retracted position or the extended position at each discrete angular position during movement of the fan beam over the range of angular positions about the patient so that the series of regular increments of effective thickness of modulation elements within the beam can be provided by selection of different combinations of the modulation elements for actuation; and (d) activating a control system communicating with each bistable actuator to independently activate the bistable actuators.

13. The method of claim 12 wherein the sequence of increasing effective thicknesses is a binary power series.

14. The method of claim 12 further wherein the thicknesses of the modulation elements are equal.

15. The method of claim 12 further including two sets of modulation elements positioned in opposition across a greatest dimension of the cross-sectional area of the fan beam.

16. The method of claim 12 wherein the modulation elements of an array are of uniform material and have different thicknesses within the beamlet cross-sectional area when in the extended position providing different reductions in ion beam energy.

17. The method of claim 12 wherein the modulation elements of an array have different densities providing different reductions in ion beam energy.

18. The method of claim 12 further wherein the bistable actuators of an array may in combination, stop transmission of the ion beam and the bistable actuators duty cycle modulate the ion beam using the bistable actuators to provide intensity modulation of the ion beam.

19. The method of claim 12 wherein a distance between the extended position and the retracted position is equal to a length of the beam cross-sectional area covered by the modulation element when in the extended position.

* * * * *